United States Patent
Jensen

(10) Patent No.: US 7,878,707 B2
(45) Date of Patent: Feb. 1, 2011

(54) SYSTEM AND METHOD FOR MONITORING ENVIRONMENTAL CONDITIONS

(75) Inventor: Thomas Jensen, Boise, ID (US)

(73) Assignee: Paksense, Inc., Boise, ID (US)

( * ) Notice: Subject to any disclaimer, the term of this patent is extended or adjusted under 35 U.S.C. 154(b) by 152 days.

(21) Appl. No.: 12/313,110

(22) Filed: Nov. 17, 2008

(65) Prior Publication Data

US 2009/0101728 A1 Apr. 23, 2009

Related U.S. Application Data

(62) Division of application No. 11/318,115, filed on Dec. 23, 2005, now Pat. No. 7,461,973.

(60) Provisional application No. 60/639,117, filed on Dec. 24, 2004.

(51) Int. Cl.
  G01K 1/08 (2006.01)
  G01K 3/00 (2006.01)
  F24F 3/14 (2006.01)
  H03M 1/34 (2006.01)
  B65B 57/00 (2006.01)

(52) U.S. Cl. ............. 374/142; 374/103; 236/44 C; 341/164; 53/507

(58) Field of Classification Search ............. 374/102, 374/103, 141, 142; 236/44 C; 341/118, 341/119, 159, 166, 164; 53/507, 508; 73/25.01, 73/25.04, 29.01, 335.02

See application file for complete search history.

(56) References Cited

U.S. PATENT DOCUMENTS

| | | | |
|---|---|---|---|
| 4,024,495 A | 5/1977 | O'Brien | |
| 4,102,194 A | 7/1978 | Eng | |
| 4,536,851 A | 8/1985 | Germanton et al. | |
| 4,567,465 A | 1/1986 | Komiya | |
| 4,669,055 A | 5/1987 | Berger et al. | |
| 5,867,809 A | 2/1999 | Soga et al. | |
| 5,969,606 A | 10/1999 | Reber et al. | |
| 6,034,607 A | 3/2000 | Vidaillac | |
| 6,217,213 B1 | 4/2001 | Curry et al. | |
| 6,297,761 B1 | 10/2001 | Barrenscheen et al. | |
| 6,411,916 B1 | 6/2002 | Pellerin | |
| 6,549,135 B2 | 4/2003 | Singh et al. | |

(Continued)

OTHER PUBLICATIONS

Integrator, Sep. 26, 2003, http://www.allaboutcircuits.com, vol. 6, Chapter 6. Accessed Jan. 25, 2008, (11 pgs).

(Continued)

Primary Examiner—Chen-Wen Jiang
(74) Attorney, Agent, or Firm—Brooks, Cameron & Huebsch, PLLC

(57) ABSTRACT

A system and method are disclosed for monitoring environmental conditions of a perishable product. The system includes an environmental sensor configured to sense one or more environmental conditions of the perishable product and an analog integrator in communication with the environmental sensor, the analog integrator being formed on a polymer substrate and including one or more tunable components. The system also includes a comparator in communication with the analog integrator and configured to change state when an output of the analog integrator reaches a selected threshold level, and a control module in communication with the comparator and the analog integrator. The control module is configured to control the operation of the analog integrator based on an output of the comparator.

7 Claims, 4 Drawing Sheets

U.S. PATENT DOCUMENTS

| | | |
|---|---|---|
| 6,771,177 B2 | 8/2004 | Alderman |
| 6,817,192 B2 | 11/2004 | Ector, Jr. et al. |
| 6,865,516 B1 | 3/2005 | Richardson |
| 6,950,028 B2 | 9/2005 | Zweig |
| 7,057,495 B2 | 6/2006 | Debord et al. |
| 7,127,943 B1 | 10/2006 | Griffiths et al. |
| 7,248,147 B2 | 7/2007 | Debord et al. |
| 7,461,973 B2 | 12/2008 | Jensen |
| 2004/0156418 A1 | 8/2004 | Debord et al. |
| 2004/0212507 A1 | 10/2004 | Zweig |
| 2004/0212509 A1 | 10/2004 | Zweig |
| 2006/0061454 A1 | 3/2006 | Debord et al. |
| 2006/0132698 A1 | 6/2006 | Furlani et al. |
| 2007/0273507 A1 | 11/2007 | Burchell et al. |

OTHER PUBLICATIONS

Western Washington University (WWU), Parallel-Plate Capacitors, Feb. 18, 2001. Accessed Jan. 29, 2008 (4 pgs).

SYSTEM AND METHOD FOR MONITORING ENVIRONMENTAL CONDITIONS

PRIORITY INFORMATION

This application is a Divisional of U.S. patent application Ser. No. 11/318,115 filed Dec. 23, 2005, now U.S. Pat. No. 7,641,973 which claims priority to U.S. Provisional Patent Application No. 60/639,117, filed Dec. 24, 2004, the disclosures of which are incorporated herein by reference in its entirety. A notice of allowance with regard to the preceding application was mailed on Aug. 5, 2008.

BACKGROUND

Embodiments of the present disclosure relate generally to methods and apparatus for monitoring temperature, humidity, and/or other environmental or chemical analog variables. More particularly, although not exclusively, these embodiments are concerned with the detection of product abuses such as spoilage and/or the detection of the level of freshness or environmental abuses of products, equipment or consumable items.

As an introduction to the problems solved by the present application, it is generally desirable in the art of making smart labels and smart packaging products to be able to measure the integral of temperature, humidity, or other variable over time. Such an integration measurement can be used to indicate a degree of exposure to undesirable environmental conditions. Time-Temperature Integration (TTI) and Time-Humidity Integration (THI) are two such valuable metrics used to determine product abuses or levels of freshness.

To accomplish such measurements, it is known in the art that a high degree of accuracy can be obtained using an Analog to Digital Converter (ADC), together with a processing logic unit that performs floating-point algorithms. Alternately, a microprocessor, a Programmable Logic Device (PLD) or a Digital Signal Processor (DSP) type of processing platform can be used.

When considering the cost of goods required to build such processing circuitry into smart labels and smart packages, even at the smallest levels of integration (deep sub-micron), using fully custom Application Specific ICs (ASICs), the cost of goods is too high to be applicable in a typical packaging situation. Cost sensitivities drive the need for lower-cost and lower-power circuitry for smart label and smart packaging devices.

SUMMARY

The circuit architecture and fabrication method of the present application provides signal processing using an analog integration method, with circuit elements built directly onto a substrate comprising a polymer, such as, for example, Polyethylene (PET) or Polyamide.

It is understood in the art that circuit elements such as transistors, resistors, capacitors, LEDs, and high grade conductors can be fabricated directly upon PET substrates using ink-jet printing methods. This disclosure applies these methods, in combination with the use of silicon-based circuits, to achieve a low-cost temperature and humidity integration and indication circuits.

An analog circuit can drift and lose accuracy when used to measure the integrated value of a variable (such as temperature or humidity) over long periods of time. Due to tolerance problems with analog components, it is difficult to gain degrees of accuracy greater than about 0.1% using off-the-shelf chip resistors and capacitors. Parts of the circuit can be tuned, and precision component tolerances can be specified, but at increased expense.

The apparatus disclosed in the present application can be trimmed by laser cutting to achieve high accuracy. This, in combination with other aspects of the sampling and counting methods used, result in an accurate method of performing the long-term integrations required to suit the smart label and smart packaging applications.

In one embodiment, an integrator comprises a polymer substrate and an operational amplifier comprising a first input terminal, a second input terminal, and an output terminal. The integrator further comprises an accumulator formed on the polymer substrate and connected between the first input terminal and the output terminal of the operational amplifier.

In another embodiment, a system is disclosed for monitoring environmental conditions of a perishable product. The system comprises an environmental sensor configured to sense one or more environmental conditions of the perishable product and an analog integrator in communication with the environmental sensor, the analog integrator being formed on a polymer substrate and including one or more tunable components. The system further comprises a comparator in communication with the analog integrator and configured to change state when an output of the analog integrator reaches a selected threshold level, and a control module in communication with the comparator and the analog integrator. The control module is configured to control the operation of the analog integrator based on an output of the comparator.

In another embodiment, a system comprises a humidity sensor coupled to a first analog integrator and a temperature sensor coupled to a second analog integrator. The system further comprises a first comparator coupled to the first analog integrator and a second comparator coupled to the second analog integrator. The system further comprises an analog-to-digital converter coupled to the humidity sensor and the temperature sensor, and a control module coupled to the first and second analog integrators, the first and second comparators, and the analog-to-digital converter.

In another embodiment, a method of tuning a system for monitoring environmental conditions of a perishable product comprises fabricating a capacitor comprising a first capacitive plate formed on an upper surface of a polymer substrate and a second capacitive plate formed on a lower surface of the polymer substrate, the first and second capacitive plates comprising a capacitive plate material. The method further comprises removing capacitive plate material while measuring the capacitance of the capacitor until a selected capacitance is reached, and incorporating the capacitor into an analog integrator circuit configured to receive an input signal from an environmental sensor capable of monitoring one or more environmental conditions of the perishable product.

These and other embodiments of the present application will be discussed more fully in the detailed description. The features, functions, and advantages described herein can be achieved independently in various embodiments of the present application, or may be combined in yet other embodiments.

DETAILED DESCRIPTION

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments may be utilized and that various changes may be made without departing from the spirit and scope of the present invention. The following detailed description is, therefore, not to be taken in a limiting sense.

Figure 1:
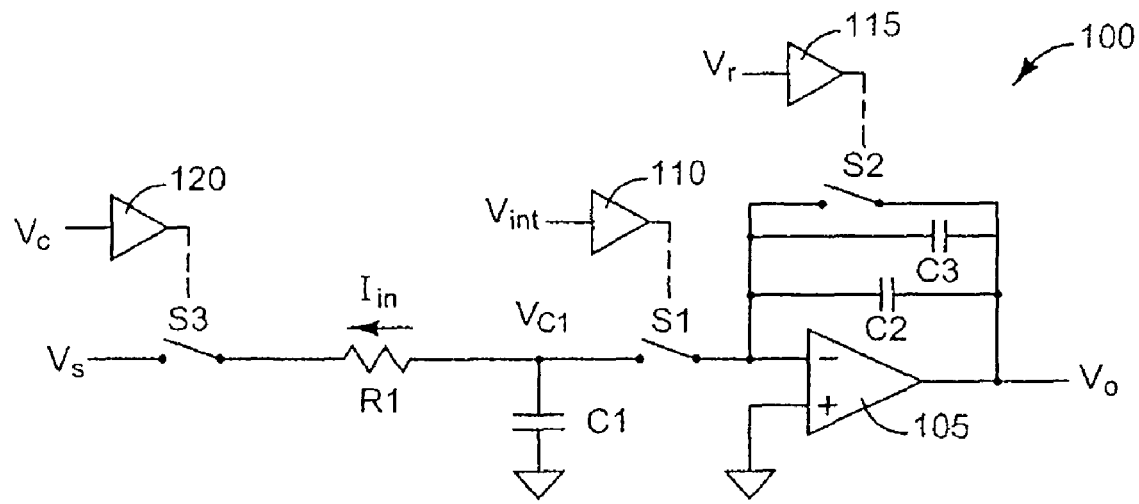
FIG. 1 is a schematic diagram of an integrator circuit in accordance with one embodiment of the present application.

Depicted in FIG. 1 are the circuit elements of an analog integrator 100 that provides sampling and integration of an input signal, $V_s$, received from an environmental sensor, such as, for example, a temperature sensor or a humidity sensor. The integrator 100 preferably allows precision measurement of low input currents that are accumulated to an accurate total charge. In some embodiments, the integrator 100 employs an operational amplifier 105 with a low input bias current. The value of resistor R1 can be selected to set the gain of operational amplifier 105 at a desired level.

Capacitor pair C2/C3 form an integrating capacitor (accumulator) that stores charge at a greater or lesser rate, based upon the input current of the operational amplifier 105. This accumulated charge, in turn, produces the output analog voltage level $V_o$, according to the following equation:

$$V_o = -\frac{1}{C_{int}} \int I_{in}(t)dt.$$

In this equation, $C_{int}$ is the combined capacitance of C2 and C3, and $I_{in}$ is the input current to the operational amplifier 105.

The arrangement and sequencing of analog switches S1 through S3 provides control of the integrator 100, as described below in connection with Table 1. In the illustrated embodiment, S1 is controlled by an integration control signal, $V_{int}$, S2 is controlled by a reset control signal, $V_r$, and S3 is controlled by a charge control signal, $V_c$. These control signals can be generated by any suitable control module, such as, for example, a logic circuit or a microcontroller. In the illustrated embodiment, the control signals are amplified by drivers 110, 115, 120, which can be integrated into the analog switches S1 through S3.

In some embodiments, capacitor C1 is of a small capacitance, e.g., tens of picofarads. When beginning from a discharged state, the charge voltage of C1 quickly rises to the level of $V_s$, the sensor voltage, whenever S3 is closed. When the integrator 100 is sequenced, the small charge from capacitor C1 is transferred to pair C2/C3. C2 is of a much larger capacitance than C1 or C3, e.g., on the order of tens of microfarads. The C2/C3 pair can contain on the order of one-half to one million samples from C1 and still not be fully charged to the negative voltage rail. In some embodiments, C3 comprises a trimming capacitor in parallel to C2. The function of C3 will be described further below.

Sensors can be connected in such a way as to sink or source current from the input terminal of the operational amplifier 105. This causes a positive or negative integration ramp voltage on C2/C3, accordingly. The configuration shown in FIG. 1 sources current and thereby produces a negative integration ramp.

Table 1 below shows four operating states of the integrator 100.

TABLE 1

| | | Integration States | | | |
|---|---|---|---|---|---|
| Step | State | S1 | S2 | S3 | Description |
| 1 | 4 | 0 | 0 | 1 | Charge C1 |
| 2 | 1 | 1 | 0 | 0 | Transfer C1 charge to C2/C3 |
| 3 | 0 | 0 | 0 | 0 | Off/Hold C2/C3 |
| R | 2 | 0 | 1 | 0 | Reset C2/C3 |

In typical operation, a series begins by charging C1 (Step 1), transferring the charge to C2/C3 (Step 2), then holding the charge for a relatively long period (Step 3) before taking another reading. In this way, sparse samples can be taken, and their aggregate value accumulated. The output $V_o$ can be sampled, or preferably it can be fed into a comparator circuit (not shown).

The comparator can be made to change state when $V_o$ reaches a preset level, and this can trigger a Reset (Step R) of the integrator 100. The occurrence of the trigger event indicates a fixed aggregate level of sensor input, which is proportional to net charge. When measuring temperature, for example, a trigger event indicates that a certain number of net calories of heat have been measured.

Figure 2:
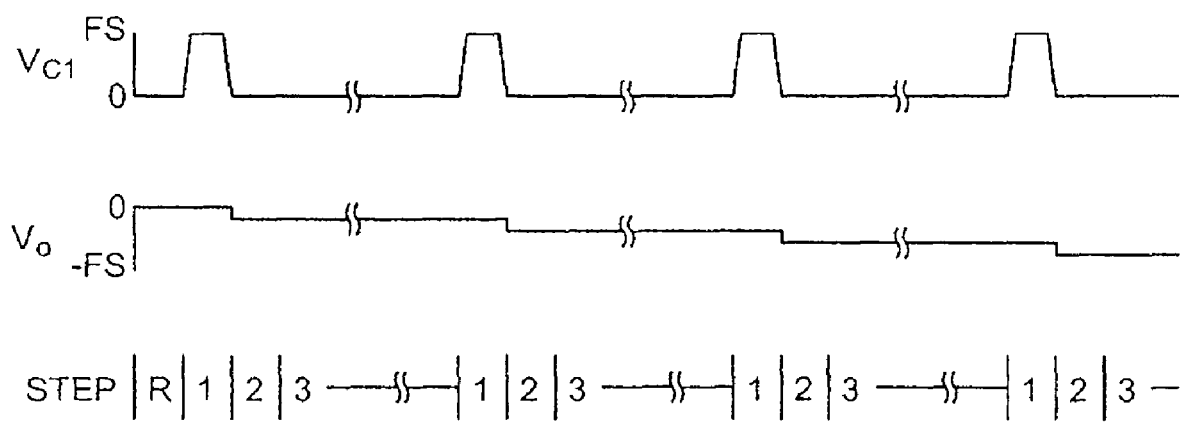
FIG. 2 is a timing diagram depicting the operation of the integrator circuit shown in FIG. 1.

FIG. 2 is a timing diagram showing the operation of the integrator 100 illustrated in FIG. 1. As illustrated in FIG. 2, $V_o$ drops slightly with each transfer of energy from C1. In the figure, FS and −FS represent the full-scale values of $V_{C1}$ and $V_o$, respectively. If the sensor voltage, $V_s$, is lower due to a lower temperature, then the integration rate will be slower.

In some embodiments, capacitors C1 and C3 are constructed in a manner such that their capacitance can be precisely set in a high-speed fabrication process. C1 and C3, if trimmed to accurate capacitance values, will provide a reliable basis for aggregate measurement of an integral of sensor output level.

Figure 3:
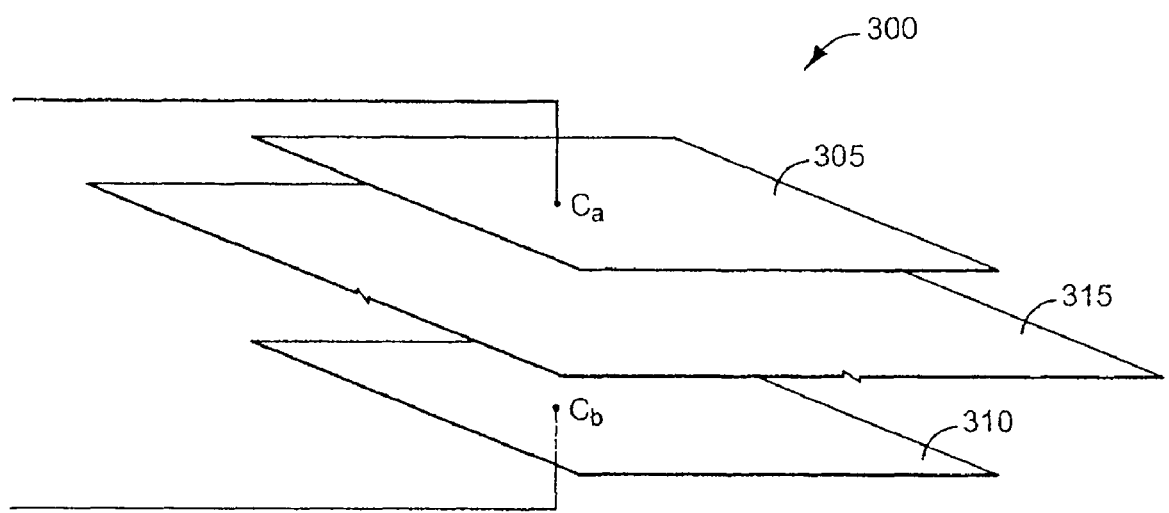
FIG. 3 depicts an isometric view of a capacitor in accordance with one embodiment of the present application, shown with layers separated for identification.

FIG. 3 depicts an isometric view of a capacitor 300 in accordance with one embodiment of the present application, shown with layers separated for identification. The exemplary capacitor 300 can be constructed for use as C1 or C3 in the integrator 100 of FIG. 1. In some embodiments, capacitor 300 comprises an upper capacitive plate 305 and a lower capacitive plate 310 separated by a dielectric layer 315. The capacitive plates 305, 310 may comprise any suitable capacitive material, such as, for example, metal. In some embodiments, the capacitive plates 305, 310 comprise conductive material formed as layers of laminated, metallized polyester film, such as, for example, Mylar®. The polyester film can be metallized with any suitable metal, such as, for example, aluminum, silver, gold, etc. Dielectric layer 315 may comprise any suitable dielectric material, such as, for example, PET, polyamide, polypropylene, etc.

In some embodiments, capacitor 300 can be built using a die-cut, roll-to-roll sheet lamination process, in which capacitor 300 can also be trimmed to a set capacitance via a closedloop capacitor tuning process. In such a process, plate material is removed as measurements are made in real-time, until the capacitance falls to a given target capacitance. Typically, a capacitance measurement instrument is connected across the capacitive plates 305, 310 and a cutting device such as a robotic laser is positioned and activated to remove precise amounts of aluminum. Further measurements and smaller cuts/holes are made until the desired capacitance is reached. Capacitive sheets may also be pleated and stacked on top of one another to increase total capacitance, and trimmed to set values in a similar manner. As a result of establishing a precise capacitance for capacitor 300, the accuracy of the integration that the integrator 100 illustrated in FIG. 1 can perform is advantageously improved.

By using the circuit construction and methods described above in a smart package or smart label product, it is possible to reduce the complexity of the silicon circuitry and to provide features of a circuit directly on a polymer substrate, such as, for example, PET, Mylar®, polyamide, etc. The electronics that can be printed and/or laminated include sensors, resistors and capacitors. The adaptation of a precision integrator using printed and laminated components provides a higher degree of benefit in its accuracy at lower total cost, as compared to conventional circuits, which consist of silicon-based circuits plus thick-film passive components that are soldered onto printed wiring boards.

Some of the materials used in printing electronic components on substrates are as follows: (a) conductors: organic inks such as PEDOT and Polyanilene (PAni) conduct electron current effectively (approximately 100 S/cm conductivity); (b) semiconductors: conjugated polymers such as Poly-3-alkylthiophene (P3AT) Polythiophene and Poly(3-hexylthiophen) can be dispensed in a solution form, as used in semiconductive inks; (c) insulators/barriers: insulating polymers, such as PMMA, are used for insulation layers and/or barrier formation. Sensors can be constructed from metallic (such as silver) sensing compounds that are deposited between two conductive electrodes on the substrate. All of these chemicals can be formulated into inks to be sprayed from ink-jet nozzles or plotted via micro-pen onto Polyethylene (PET) substrates at room temperatures, in semi-clean or clean environments.

Figure 4:
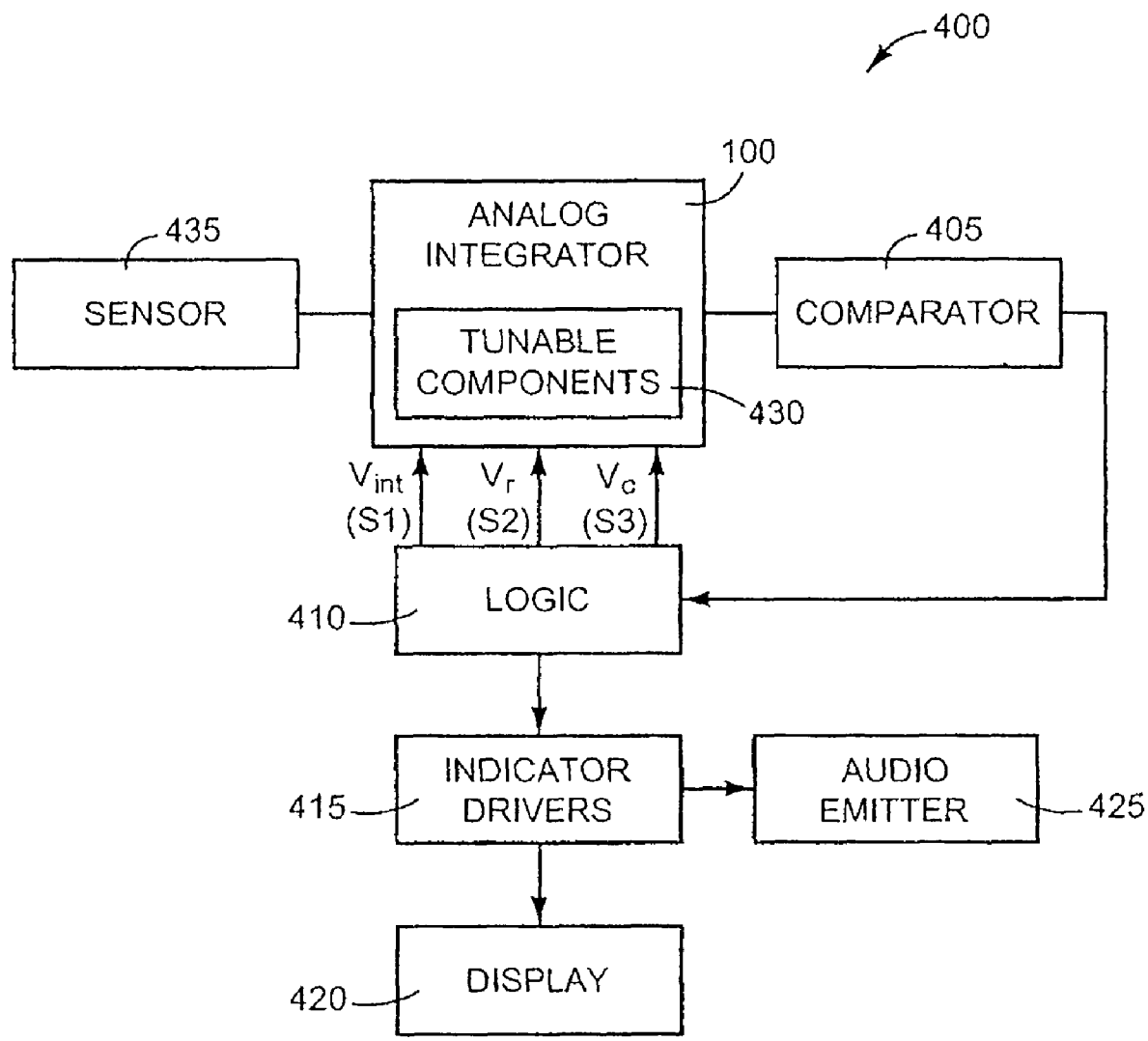
FIG. 4 is a schematic diagram of an environmental monitoring system in accordance with one embodiment of the present application.

FIG. 4 is a schematic diagram of an environmental monitoring system 400 in accordance with one embodiment of the present application. In the illustrated embodiment, the integrator 100 comprises one or more tunable components 430, such as capacitor 300 described above. In operation, integrator 100 receives an input signal, $V_s$, from an environmental sensor 435 and provides an output signal, $V_o$, to a comparator 405. When a comparison target level is reached, a logic circuit 410 sends a reset control to the integrator 100 and at the same time tallies the count of thresholds that were reached. When a target number of threshold counts are reached, the indicator drivers 415 can drive alarm indications to the display 420 or audio emitter 425. A battery and voltage converter (not shown) can be used to supply power to the system 400.

Figure 5:
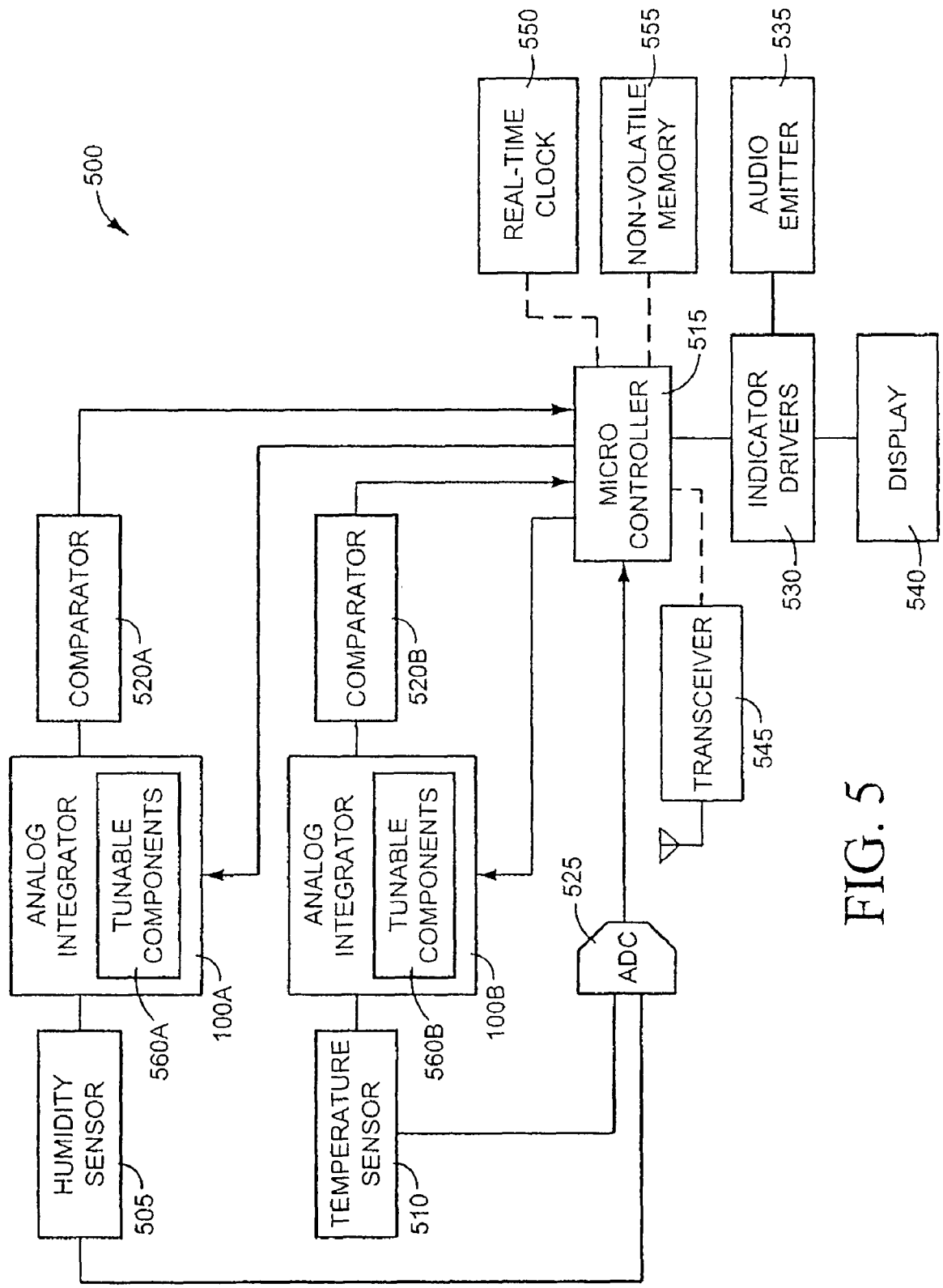
FIG. 5 is a schematic diagram of an environmental monitoring system in accordance with an alternative embodiment of the present application.

FIG. 5 is a schematic diagram of an environmental monitoring system 500 in accordance with an alternative embodiment of the present application. In the embodiment illustrated in FIG. 5, system 500 comprises two integrators 100A, 100B, each of which includes one or more tunable components 560A, 560B, such as capacitor 300 described above. The first integrator 100A is used to integrate the sensor voltage of a humidity sensor 505, and the second integrator 100B is used to integrate the sensor voltage of a temperature sensor 510. The system 500 further comprises a microcontroller 515 that receives inputs from the outputs of the two comparators 520A, 520B, and also receives input from a two-channel ADC 525 that monitors each sensor 505, 510 directly. System 500 is capable of programmatic control of integration and of indicator drivers 530, which can drive alarm indications to the display 535 or audio emitter 540. System 500 is also capable of programmatic control of such peripheral devices that can also be incorporated into the smart label or package, such as, for example, a data transceiver 545, a real-time clock 550, and/or a non-volatile memory 555. A battery and voltage converter (not shown) can be used to supply power to the system 500.

The systems and methods described above can be used to monitor environmental conditions of a wide variety of perishable products, such as meat, poultry, seafood, dairy products, cosmetics, chemicals, etc. These systems and methods can advantageously be incorporated into various labels, tags, packages, and/or packaging materials used in connection with such perishable products. As described above, these systems and methods can lead to significant cost savings over conventional circuits used in existing smart packaging and/or smart labeling products.

Although this invention has been described in terms of certain preferred embodiments, other embodiments that are apparent to those of ordinary skill in the art, including embodiments that do not provide all of the features and advantages set forth herein, are also within the scope of this invention. Accordingly, the scope of the present invention is defined only by reference to the appended claims and equivalents thereof.

What is claimed is:

1. A system comprising:
    a humidity sensor coupled to a first analog integrator;
    a temperature sensor coupled to a second analog integrator;
    a first comparator coupled to the first analog integrator;
    a second comparator coupled to the second analog integrator;
    an analog-to-digital converter coupled to the humidity sensor and the temperature sensor; and
    a control module coupled to the first and second analog integrators, the first and second comparators, and the analog-to-digital converter.

2. The system of claim 1, wherein the first and second analog integrators include one or more tunable components.

3. The system of claim 1, wherein the first and second analog integrators are fabricated on a polymer substrate.

4. The system of claim 1, wherein the control module comprises a microcontroller.

5. The system of claim 1, further comprising one or more indicator drivers coupled to the control module.

6. The system of claim 5, further comprising a display and/or audio emitter coupled to the indicator drivers.

7. The system of claim 1, further comprising a transceiver, real-time clock, and/or non-volatile memory coupled to the control module.

* * * * *